United States Patent
Hinkel (10) Patent No.: US 10,607,731 B2
(45) Date of Patent: *Mar. 31, 2020

(54) METHOD AND SYSTEM FOR AUTHENTICATING AND MONITORING HOME HEALTH INTERACTIONS

(71) Applicant: Jennifer M. Hinkel, San Francisco, CA (US)

(72) Inventor: Jennifer M. Hinkel, San Francisco, CA (US)

(*) Notice: Subject to any disclaimer, the term of this patent is extended or adjusted under 35 U.S.C. 154(b) by 317 days.

This patent is subject to a terminal disclaimer.

(21) Appl. No.: 15/614,800

(22) Filed: Jun. 6, 2017

(65) Prior Publication Data

US 2017/0270278 A1 Sep. 21, 2017

Related U.S. Application Data (63) Continuation of application No. 13/911,623, filed on Jun. 6, 2013, now Pat. No. 9,703,931.

(60) Provisional application No. 61/656,271, filed on Jun. 6, 2012.

(51) Int. Cl.
| | |
|---|---|
| *G06Q 50/20* | (2012.01) |
| *G06F 19/00* | (2018.01) |
| *G16H 15/00* | (2018.01) |
| *G06Q 50/24* | (2012.01) |
| *G16H 10/60* | (2018.01) |

(52) U.S. Cl.
CPC ......... *G16H 15/00* (2018.01); *G06F 19/3418* (2013.01); *G06Q 50/24* (2013.01); *G16H 10/60* (2018.01)

(58) Field of Classification Search
CPC ..... G06F 19/3418; G06Q 50/24; G16H 15/00

USPC .......................................................... 705/3
See application file for complete search history.

(56) References Cited

U.S. PATENT DOCUMENTS

| | | | |
|---|---|---|---|
| 7,249,036 B2 * | 7/2007 | Bayne | A61B 5/411 705/2 |
| 7,382,255 B2 | 6/2008 | Chung | |
| 8,284,024 B2 | 10/2012 | Toleti et al. | |
| 8,380,542 B2 | 2/2013 | Wons et al. | |
| 2004/0128162 A1 * | 7/2004 | Schlotterbeck | G06F 19/325 705/2 |

(Continued)

OTHER PUBLICATIONS

Kinnser Agency Manager Features, Kinnser Software, Inc., printed from internet, Jun. 3, 2013, http://www.kinnser.com/home-care-software/home-health-agency-manager/features/.

*Primary Examiner* — Hiep V Nguyen
(74) *Attorney, Agent, or Firm* — Fox Rothschild LLP (57) ABSTRACT

A system uses a multi-pass authentication method to authenticate the presence of a health care provider co-located with an assigned patient at a specific time and in a specific place that includes a data reader and transmitter with particular capabilities held by the health care provider, a token held by the patient, and a back-end database and internet-based interface. The system includes an object that includes a wirelessly detectable patient identification (ID) and an electronic device. The electronic device includes a provider ID and is configured to receive the patient ID from the object, retrieve, from a database, healthcare intervention data. The electronic device selectively locks and unlocks access to clinical data recording functions of the electronic device based on the healthcare intervention data.

20 Claims, 3 Drawing Sheets

(56) References Cited

U.S. PATENT DOCUMENTS

2012/0166680 A1* 6/2012 Masoud ............ A61N 1/37235
 710/8
2012/0232929 A1 9/2012 Experton

* cited by examiner

METHOD AND SYSTEM FOR AUTHENTICATING AND MONITORING HOME HEALTH INTERACTIONS

RELATED APPLICATIONS AND CLAIM OF PRIORITY

This application claims priority to and is a continuation of U.S. patent application Ser. No. 13/911,623, filed Jun. 6, 2013, which claims priority to U.S. Provisional Patent Application No. 61/656,271, filed Jun. 6, 2012, the disclosures of which are hereby incorporated by reference in their entirety.

BACKGROUND

This disclosure is related to methods and systems for authenticating and monitoring home health interactions between a provider of a home health service and a patient.

The market for delivery of home health services in the United States is estimated to reach more than $136.1 billion by the year 2020. Challenges in the delivery of this type of services include tracking and monitoring of a geographically dispersed workforce that cannot be directly supervised. Significant error and fraud in the recording of home health interactions has been reported, with one example being a case that the US Department of Justice has brought against home health providers in Texas for more than $374 million (March 2012) with allegations of defrauding Medicare and Medicaid. Patient health outcomes can also be put at risk if a home health provider fails to be present at a scheduled time, and no current system exists to alert third parties when a patient's health care provider does not arrive. As a result, a patient could be left alone, or could fail to receive a service that has been scheduled and/or paid for.

SUMMARY

A method, device, and system for authenticating and monitoring home healthcare interactions are disclosed.

In an embodiment, a system includes an object that includes a wirelessly detectable patient identification (ID) and an electronic device. The electronic device includes a provider ID and is configured to receive the patient ID from the object, retrieve, from a database, healthcare intervention data that includes an expected patient ID and an expected provider ID for a scheduled healthcare intervention, and compare the object's patient ID to the expected patient ID and the device's provider ID with the expected provider ID. The electronic device is also configured to unlock access to clinical data recording functions of the electronic device only if the object's patient ID matches the expected patient ID and the device's provider ID matches the expected provider ID. The electronic device otherwise locks out access to the clinical data recording functions.

In another embodiment, an electronic device for authenticating a scheduled healthcare intervention includes a processor, a network interface, a short-range communications component, and a computer readable medium for storing a provider ID and program instructions. The program instructions, when executed, cause the processor to perform a method for authenticating and monitoring home healthcare interactions.

In a method embodiment, the electronic device receives a patient ID from a wireless identification enabled object using the short-range communications component. The electronic device retrieves, from a database, healthcare intervention data that includes an expected patient ID and an expected provider ID for a scheduled healthcare intervention. The electronic device compares the expected patient ID with the received patient ID and the expected provider ID with the stored provider ID. If either the expected patient ID does not match the received patient ID or the expected provider ID does not match the stored provider ID, the electronic device engages a lock on the electronic device that prevents the recording of clinical data, generates an exception report, and generates and transmit via the network interface a message that informs a third party of the exception report. Only if the expected patient ID matches the received patient ID and the expected provider ID matches the stored provider ID, disengage the lock on the electronic device to permit the recording of clinical data.

DETAILED DESCRIPTION

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to."

For the purposes of this document, an "electronic device" refers to a device that includes a processor and non-transitory, computer-readable memory. The memory may contain programming instructions that, when executed by the processor, cause the device to perform one or more operations according to the programming instructions. Examples of electronic devices include personal computers, gaming systems, televisions, and portable electronic devices such as smartphones, personal digital assistants, cameras, tablet computers, laptop computers, GPS navigation devices, media players and the like.

A method and system for authenticating the presence of home health providers at a specified time and place with the assigned patient is described. The system may alert third parties of exceptions in real time and help to reduce fraud and error. The system is a multi-pass authentication system and interaction recording system for reducing medical documentation fraud and error and for facilitating the recording of provider/patient interactions, for example in the delivery of home health or remote services.

In an embodiment, a reading/transmitting electronic device (such as a smart phone) may be provided to a health care provider, The device may include a secured software application (referred to herein as an "app") that includes security in the form of a personal identification number (PIN), biometrics, gestures, or other security measures designed to prevent unauthorized access to the app; equipped with near field communication (NFC) or other short range wireless detection capability (e.g. Bluetooth®, radio frequency identification (RFID), and the like), global position system (GPS) capability or another location service capable of determining the location of the device; a time stamp/clock; and wireless transmission and reception capabilities to send data on demand/when triggered and at regular set intervals. The device also includes a mechanical, electronic, and/or software lock that is capable of preventing or blocking some or all of the device's functions. The lock may be implemented through the secured app described above, through a separate application, or within the operating system of the device. When the lock is implemented, a user of the device may be restricted from accessing one or more functions of the device, such as a software app that enables the health care provider to receive and transmit clinical data relating to a patient. When the lock is unlocked, the device may permit the health care provider to transmit and access such data.

The system also may include a wirelessly detectable object (such as a card, tag, or sticker) that may be provided to a patient. For simplicity, such an object may be referred to as a "tag." A data storage facility such as a database is capable of holding the following information: identification (ID) of a health care provider in possession of the electronic device; ID of a patient holding the tag; intended/scheduled time and duration of health care intervention to be delivered; and intended/scheduled location of health care intervention to be delivered. The system can also include additional receiving devices that gather information from the database, i.e. third party users/subscribers and devices such as computers or additional input devices (smartphone, tablet) that enter data into database via a software application. Each ID may be any token that the system can use to uniquely identify a corresponding entity, such as a passcode, an electronic signature, or other token.

An embodiment of the system may implement a workflow that includes any or all of the following steps: Using an internet-based/web-based portal accessed on a computer, smartphone, tablet, or other electronic device, a registered user enters into the database (or pulls from an established data source) the following data points: ID of a health care provider; ID of a patient; and health care intervention data such as scheduled/Intended time(s) and/or duration(s) of health care interventions to be delivered by provider to patient, and scheduled and/or intended location of health care intervention to be delivered.

Each health care provider holds a reading and transmitting device with an application as described above. Each patient holds a readable short range communication-enabled object as described above. The phrase "holding" does not necessarily mean that the person physically holds the device, but that the device is in proximity to and can be moved by the person. For example, the device may be in the person's pocket, briefcase, or in a nearby location. When the provider's device and the patient's object come into contact via electronic communication, the provider's device sends the following data points to the database as described above:

A—ID of the health care provider or of the electronic device;

B—ID of the patient or of the tag;

C—Current time as indicated by electronic device; and

D—Current location as indicated by electronic device.

If some or all A, B, C, and D do not match the data held in the database within parameters circumscribed by an established decision engine, the lock as described above is not unlocked and an exception report may be generated. As a consequence of the exception report, an electronic message or other transmission (email, telephone call, SMS text message) may be generated and sent to one or more subscribing parties such as health care providers, management of health care providers, patient, or designated representatives of patient to alert them to the exception and to prompt them to take an action to remedy the exception. The subscribing parties also may be using electronic devices such as those described above. Note that any combination of A, B, C, or D may be defined to trigger the lock, depending on user requirements.

If s all of A, B, C, and D (or optionally a particular subset of those parameters) do match the data held in the database within parameters circumscribed by an established decision engine, the lock as described above is unlocked and an additional software application on electronic device, or additional features of the security application, can be initiated. Through the application, the health care provider can then record administrative and/or clinical data elements relevant to the health care intervention. If the health care intervention has a designated time duration entered into the database, the transmitting electronic device will at a regular interval transmit data elements C and D to database to check against the previously entered time and duration. If at any time elements C and D do not match the time and duration elements previously entered into database, the system triggers the lock to generate an exception report, triggering messages to external devices and a locking of the ability to use the electronic device to continue to record or transmit data regarding that health care interaction. Note that any combination of A, B, C, or D may be defined to unlock the device/app, depending on user requirements.

Figure 1:
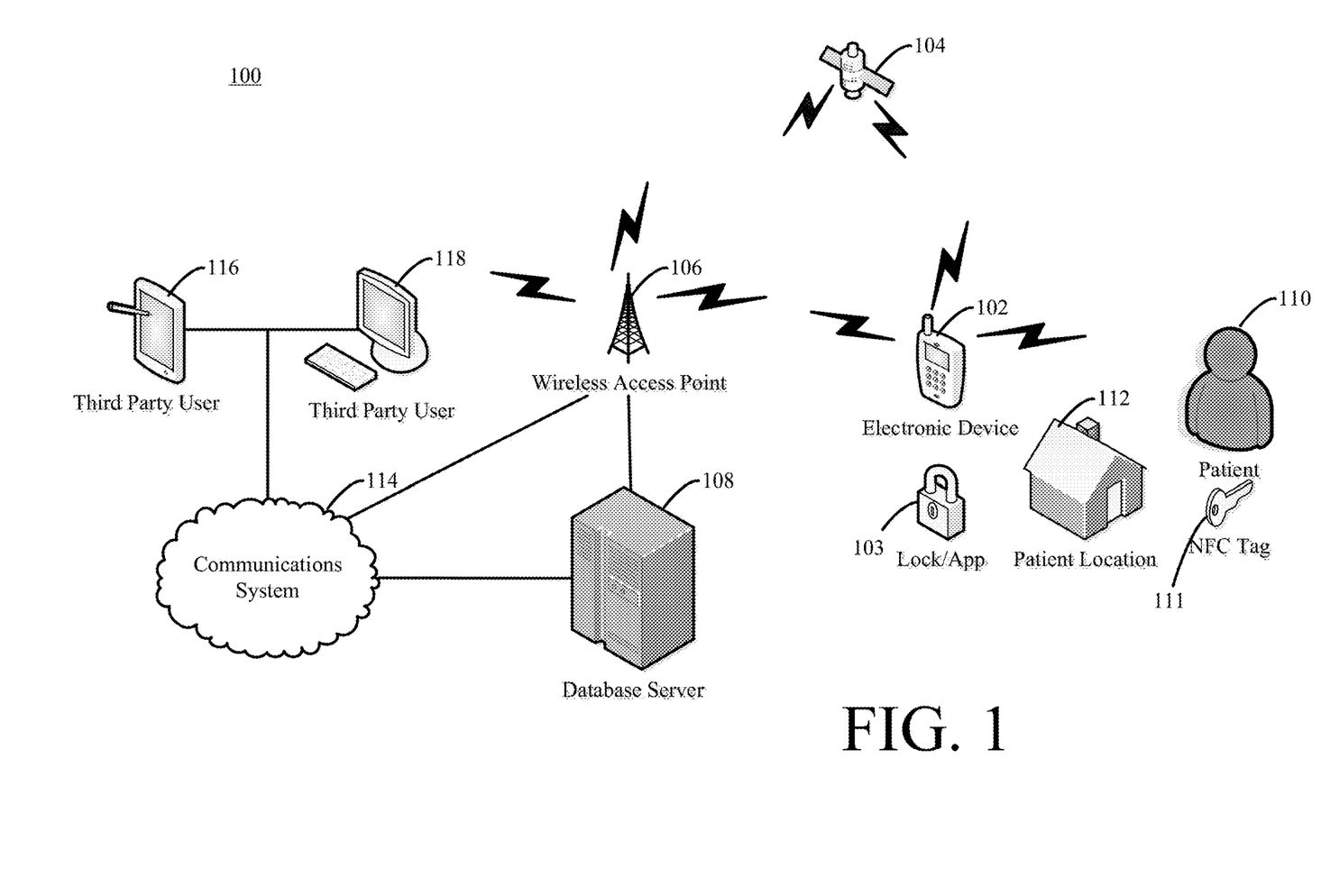
FIG. 1 is a system diagram of a system in accordance with an aspect of the present disclosure.

FIG. 1 provides a diagram of a system in accordance with an embodiment of the present disclosure. The system includes an electronic device 102, which may include a lock and/or app 103. As described above, the electronic device 102 may include a software app and/or a locking mechanism that renders some or all of the functions of the device inoperable should certain conditions arise. The system 100 also includes patient 110 which may have tag 111. As described above, the tag 111 includes a wirelessly detectable component that is readable by the electronic device 102. Patient 110 is located at patient location 112. The electronic device 102 may have a transceiver (not shown) that enables it to communicate with a GPS satellite 104 and/or a wireless access point 106. Wireless access point 106 can be any wireless transceiver including a wireless router, base station, NodeB, eNodeB, or any other wireless communications apparatus that allows access to a computer/communications network. Through the wireless access point 106 and the transceiver (not shown), the electronic device 102 may be in communication with a database server 108. In alternative embodiments, database server may be an app, service, or process on the electronic device 102. A communications system or network may be connected to wireless access point 106 and/or database server 108. The communication system is also in communication with third party user 116 and third party user 118, collectively subscribing parties.

Figure 2:
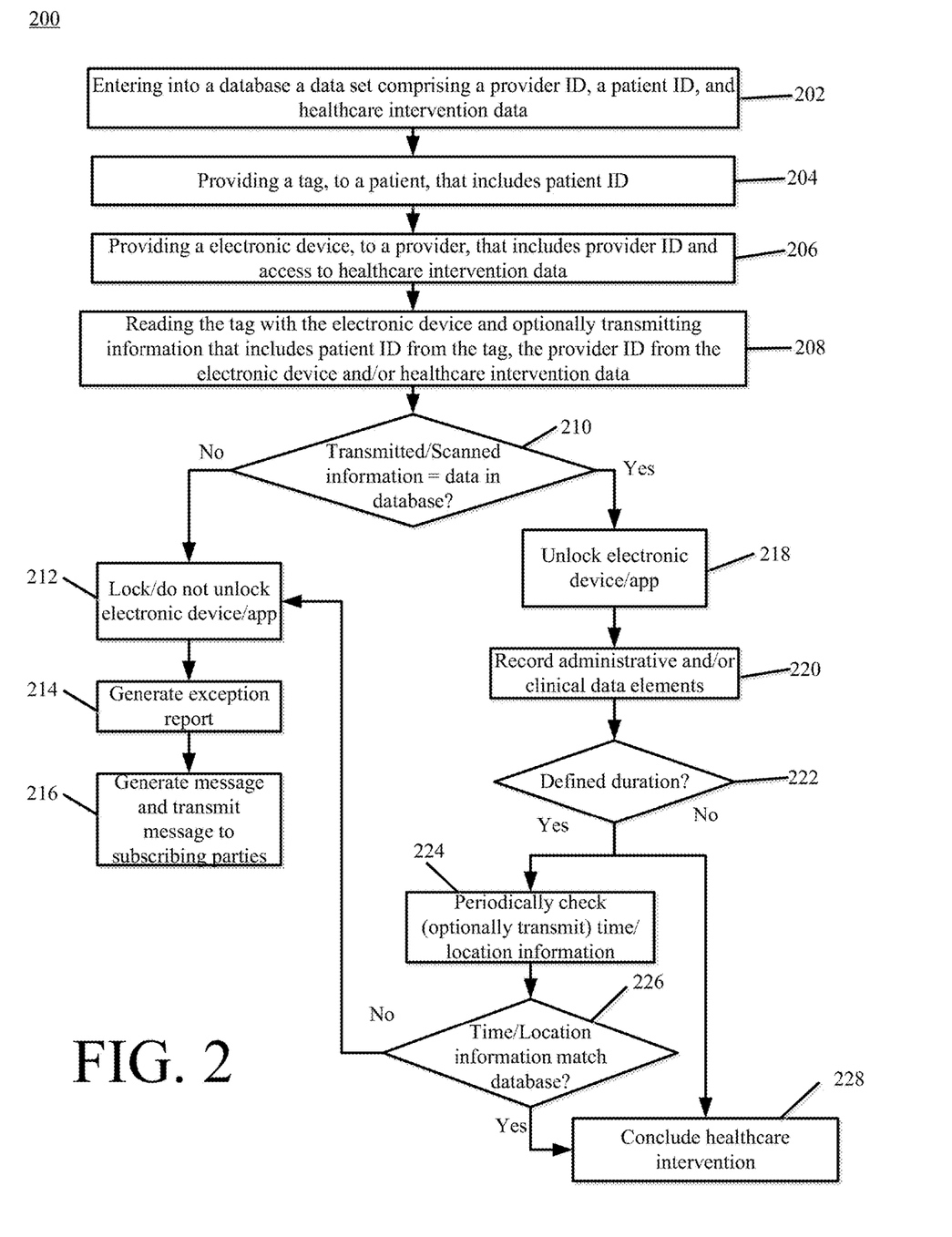
FIG. 2. is a flow chart of a process in accordance with an aspect of the present disclosure.

FIG. 2 provides a flowchart illustrating a process 200 in accordance with the present disclosure. Process 200 begins with step 202 where data is entered into a database that includes at least a provider ID, a patient ID, a scheduled and/or intended time and/or duration of a healthcare intervention, and a scheduled and/or intended location of the healthcare intervention. The provider ID can be any information that is capable of identifying the individual providing healthcare services, e.g. an employee identification number. Likewise, the patient ID can be any information that is capable of identifying the individual that is provided healthcare services by the provider. The scheduled time, duration and location, any or all of with may be collectively referred to as the healthcare intervention data, represent a time, duration, and location for a scheduled healthcare intervention. For example, data may be entered that describes a scheduled home visit by healthcare provider X to patient Y at patient Y's home on Tuesday May 23, 2012 at 10 am with a duration of one hour. This information may be entered into the database through automatic procedures or manual data entry.

Once the data has been entered into the database, the process 200 continues to step 204 where a tag is provided to a patient. The tag can be any radio frequency identification (RFID) or near field communication (NFC) capable object. The tag is encoded with a patient ID. In step 206, an electronic device is provided to a healthcare provider. The electronic device may be a smartphone, tablet computer, or other computing device. The electronic device is described in detail below in reference to FIG. 3. The electronic device is loaded with a mobile application (app) that is configured to perform a series of functions for a healthcare provider operating the device. The app can be include a security mechanism that is required for activation, meaning that the provider must enter a code, number, biometric identifier, password and/or other security token to operate the app. The token may be the provider ID or some other code that identifies the user (provider). Alternatively, the provider ID may be stored on the phone. The app also includes access to healthcare intervention data, described above. This data can be stored on the device or can be accessed through a data network.

In step 208, the provider is able to operate the app to wirelessly detect or read a patient tag with the electronic device. This scanning can be done using the electronic device's short range communication capability. The information scanned can be the patient ID although the embodiments are not so limited. In one scenario, a start time may be stored by the electronic device when the patient ID is initially scanned. This start time may be used for calculating the duration of the healthcare intervention. The scanned patient ID, together with the provider ID, date, and time are compared, in step 210, with the information retrieved from the database. As described above, the database may include information, such as an expected patient ID, an expected provider ID, a scheduled/intended time, duration, and location, and the like. This database can be located on a network server or be stored on the electronic device. If the patient ID, provider ID, date, and time do not match what was previously entered into the database (210: No), then a mechanical, electronic, or software lock will prevent the app from being operable in step 212. This lock can limit the functionality of the app, the entire phone, or a substantial portion there of. The lock can be implemented within the same app that reads the patient tag, the app that is used to record data in step 220 below, a third app, or part of the operating system of the device. In step 214 an exception report is generated. In step 216, a message is generated and sent to subscribing third parties detailing the exception report.

If the comparison in step 210 is positive and the data matches what was previously entered into the database (210: Yes), the app and/or device is unlocked. In step 220, the provider carries out the healthcare intervention and records administrative and/or clinical data elements using the app.

In step 222, it is determined whether the healthcare intervention includes a pre-defined duration. If so (222: Yes), the app/device periodically checks date, time, and/or location data in step 224. Optionally, the app/device can transmit the data through a network. In step 226, the date, time, and location data is checked against the duration data in the database. If the data is out of range for the duration of the healthcare intervention, or if data is not received that is expected (226: No), the process continues to steps 212-216 were the app/device is locked and the exception report and third party messages are generated. If the data matches what is expected in the database (226: Yes), the provider concludes the healthcare intervention in step 228. If there is no pre-defined duration for the healthcare intervention (222: No) the process immediately proceeds to step 228.

Figure 3:
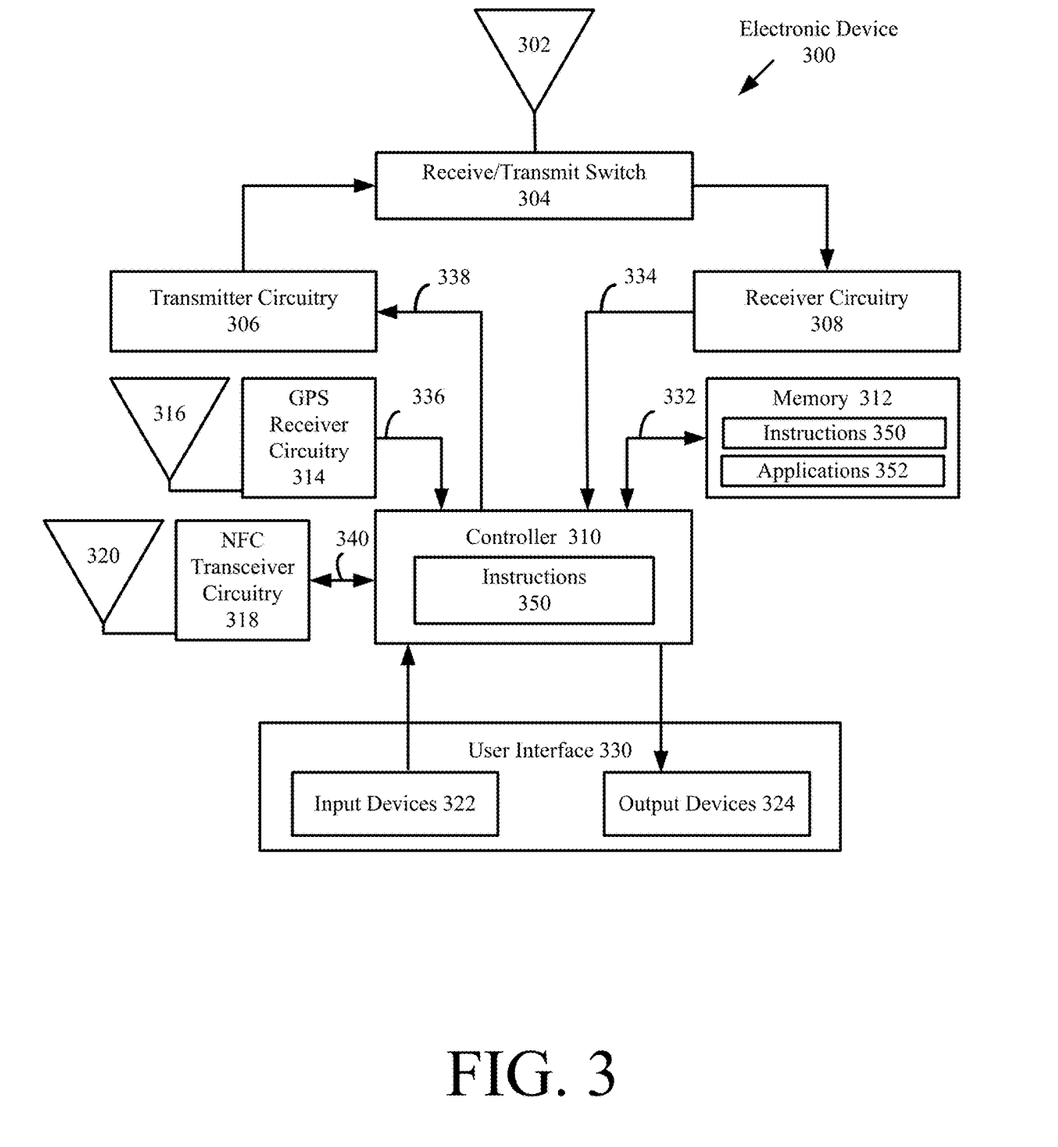
FIG. 3 is a block diagram of an electronic device in accordance with an aspect of the present disclosure.

FIG. 3 provides a diagram of an electronic device 300. As shown in FIG. 3, the electronic device 300 may include an antenna 302 or other structure for receiving and transmitting short range communications such as Radio Frequency (RF) signals. A receive/transmit (Rx/Tx) switch 304 selectively couples the antenna 302 to the transmitter circuitry 306 and receiver circuitry 308 in a manner familiar to those skilled in the art. The electronic device may include receiver circuitry 308 which demodulates and decodes the signals received from a network or wireless access point (e.g., the wireless access point 106 of FIG. 1) to derive information therefrom. The receiver circuitry 308 is coupled to a controller 310 via an electrical connection 334. The receiver circuitry 308 provides the decoded signal information to the controller 310. The controller 310 uses the decoded signal information in accordance with the function(s) of the electronic device 300. The controller 320 also provides information to the transmitter circuitry 306 for encoding and modulating information into RF signals. Accordingly, the controller 310 is coupled to the transmitter circuitry 306 via an electrical connection 338. The transmitter circuitry 306 communicates the signals to the antenna 302 for transmission to an external device.

Similarly, the electronic device may be global positioning system (GPS)-enabled for receiving location information for the device from a GPS system. An antenna 316 is coupled to GPS receiver circuitry 314 for receiving GPS signals. The GPS receiver circuitry 314 demodulates and decodes the GPS signals to extract GPS location information therefrom. The GPS location information indicates the location of the electronic device 300. The GPS receiver circuitry 314 provides the decoded GPS location information to the controller 320. As such, the GPS receiver circuitry 314 is coupled to the controller 310 via an electrical connection 336. Notably, the present invention is not limited to GPS based methods for determining a location of the electronic device 300. Other methods for determining a location of a electronic device can be used with the present invention without limitation.

The electronic device also may be enabled to support Near Field Communication (NFC). If so, an antenna 320 may be coupled with NFC transceiver circuitry 318 for transmitting and receiving NFC signals. NFC signals are used to transmit small amounts of information over a short distance by placing the device near another NFC enabled object. Transmitted information can include a patient ID, provider ID, healthcare intervention information, and the like. The embodiments of the present disclosure are not limited in this regard.

The controller 310 stores the decoded short range (e.g., RF or NFC) signal information and the decoded GPS location information in a memory 312 of the electronic device 300. Accordingly, the memory 312 is connected to and accessible by the controller 310 through an electrical connection 332. The memory 312 can be a volatile memory and/or a non-volatile memory. For example, the memory 312 can include, but is not limited to, a Random Access Memory (RAM), a Dynamic Random Access Memory (DRAM), a Static Random Access Memory (SRAM), Read-Only Memory (ROM) and flash memory. The memory 312 can also have stored therein instructions 350 and one or more software applications 352.

The software applications 352 or one or more features of the software applications may include, but are not limited to, applications operative to provide healthcare intervention data recording services; identity validation services; NFC services; telephone services, network communication services, GPS based services, navigation services, location services, position reporting services, traffic status services, operational information services, commerce services, email services, web based services, and/or electronic calendar services. As shown in FIG. 3, one or more sets of instructions 350 are also stored in the memory 312. The instructions 350 can also reside, completely or at least partially, within the controller 310 during execution thereof by the electronic device 300. In this regard, the memory 312 and the controller 320 can constitute machine-readable media. The term "machine-readable media", as used here, refers to a single non-transitory medium or multiple non-transitory media that store the one or more sets of instructions 350. The term "machine-readable media", as used here, also refers to any non-transitory medium that is capable of storing, encoding or carrying the set of instructions 350 for execution by the electronic device 300 and that cause the electronic device 300 to perform one or more of the methodologies of the present disclosure.

The controller 310 is also connected to a user interface 330. The user interface 330 is comprised of input devices 322, output devices 324, and software routines (not shown in FIG. 3) configured to allow a user to interact with and control software applications 352 installed on the computing device 300. Such input and output devices may include any input/output device which is now known or known in the future. The invention is not limited in this regard.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

As an example application of the methods and systems described above, a home health care provider may arrive at a patient's home and touch the patient's card to a smart phone. The provider, patient, time, and location may be matched against data in a database. It the data is correct, the system unlocks (i.e., authorizes the user to access) a software application on the smart phone, thus allowing the provider to enter necessary data for the billing and administration of the interaction. If the provider does not arrive in time and the card and smart phone do not touch, the app may remain locked, and the system may send electronic or telephone alerts to third parties such as the patient's family caregiver and/or the agency employing the healthcare provider.

The above-disclosed features and functions, as well as alternatives, may be combined into many other different systems or applications. Various presently unforeseen or unanticipated alternatives, modifications, variations or improvements may be made by those skilled in the art, each of which is also intended to be encompassed by the disclosed embodiments.

The invention claimed is:

1. An electronic device for securing access to and recording of healthcare information related to a healthcare intervention, the device comprising:
    a processor;
    a network interface;
    a short-range communications component;
    a computer readable medium for storing a provider identification (ID) that identifies a healthcare provider and program instructions that, when executed, cause the processor to:
        enable a software lock that prohibits the healthcare provider from using the electronic device to access, receive, or transmit any healthcare information concerning a patient's healthcare intervention;
        receive, from a wireless identification enabled object held by the patient using the short-range communications component, a patient ID that identifies a patient;
        retrieve, from a database accessed over the network interface, healthcare intervention data that includes an expected patient ID, an expected provider ID for a scheduled healthcare intervention to be performed on an expected patient associated with the expected patient ID, and expected time criteria associated with the patient's healthcare interaction;
        receive a time signal that identifies a current time;
        maintain the software lock on the electronic device that prevents recording of clinical data if the expected patient ID does not match the received patient ID, the expected provider ID does not match the stored provider ID, or the current time is not consistent the expected time criteria; and
        disengage the software lock on the electronic device to permit the recording of clinical data and completion of the healthcare intervention only if the expected patient ID matches the received patient ID, the expected provider ID matches the stored provider ID, and the current time is consistent the expected time criteria.

2. The device according to claim 1, further comprising a global positioning system (GPS) circuitry associated with the electronic device, wherein the program instructions, when executed, further cause the processor to:
    receive, from the GPS circuitry associated with the electronic device, a location signal that identifies a current location of the electronic device;
    retrieve, from the database, expected location criteria identifying where the healthcare intervention is to be performed;
    maintain the software lock on the electronic device that prevents the recording of clinical data if the expected patient ID does not match the received patient ID, the expected provider ID does not match the stored provider ID, the current time is not within the expected time criteria, or the current location is not within the expected location criteria; and
    disengage the software lock on the electronic device to permit the recording of clinical data and completion of the healthcare intervention only if the expected patient ID matches the received patient ID, the expected provider ID matches the stored provider ID, the current time is within the expected time criteria, and the current location is within the expected location criteria.

3. The device according to claim 2, wherein the program instructions, when executed, cause the processor to:
generate an exception report if the expected patient ID does not match the received patient ID, the expected provider ID does not match the stored provider ID, the current location is not within the expected location criteria, or the current time is not within the expected time criteria; and
generate and transmit via the network interface a message that informs a third party of the exception report.

4. The device according to claim 2, wherein the program instructions, when executed, cause the processor to:
generate an exception report if the scheduled time does not match the current time; and
generate and transmit via the network interface a message that informs a third party of the exception report.

5. The device according to claim 2, wherein the program instructions, when executed, cause the processor to:
generate an exception report if the current location does not match the expected location criteria; and
generate and transmit via the network interface a message that informs a third party of the exception report.

6. The device according to claim 2, wherein the expected time criteria further includes a scheduled duration, and wherein the program instructions, when executed, cause the processor to:
periodically determine a current duration for the scheduled healthcare intervention;
generate an exception report if the current duration is longer than the scheduled duration; and
generate and transmit via the network interface a message that informs a third party of the exception report.

7. The device according to claim 6, wherein the current duration comprises an amount of time that has elapsed since the scheduled time of the scheduled healthcare intervention.

8. The device according to claim 6 wherein the current duration comprises an amount of time that has elapsed since the patient ID was scanned by the electronic device.

9. The device according to claim 1 further comprising additional program instructions that, when executed after the software lock is disengaged, cause the processor to receive and record clinical data for the scheduled healthcare intervention.

10. The device according to claim 1, further comprising additional the program instructions, when executed, cause the processor to transmit, through the network interface, one or more data messages to the database, the one or more data messages including one or more of a current time, a start time, a current location, a current duration, and the clinical data.

11. A system, comprising:
an object to be held by a patient that includes a wirelessly detectable patient identification (ID); and
a provider electronic device, comprising location determining circuitry configured to determine a current location of the provider electronic device, wherein the provider electronic device includes a provider ID that is unique to a healthcare provider and is to be held by the healthcare provider, wherein the provider electronic device includes an enabled software lock that prohibits the provider electronic device from accessing, receiving, or transmitting any healthcare information concerning the patient's healthcare intervention, wherein the electronic device is configured to:
read the patient ID from the object;
receive, from the location determining circuitry associated with the electronic device, a location signal that identifies the current location of the electronic device;
receive a time signal that identifies a current time;
retrieve, from a database, healthcare intervention data that includes expected time criteria, an expected patient ID, an expected provider ID for a healthcare intervention to be performed on an expected patient associated with the expected patient ID, and expected location criteria identifying where the healthcare intervention is to be performed; and
permit access to clinical data recording functions of the electronic device by disengaging the software lock only if the object's patient ID matches the expected patient ID, the device's provider ID matches the expected provider ID, the current location is within the expected location criteria, and the current time is within the expected time criteria, otherwise maintaining the software lock and prohibiting access to the clinical data recording functions.

12. The system according to claim 11, wherein:
the expected time criteria further includes a scheduled time, a scheduled duration, and a scheduled location for the scheduled healthcare intervention, and
the electronic device is further configured to:
determine a current duration;
determine whether the current time matches the scheduled time, whether the current duration matches the scheduled duration, and whether the current location matches the scheduled duration; and
unlock access to clinical data recording functions of the electronic device by disengaging the software lock only if the current time matches the scheduled time, the current duration matches the scheduled duration, and the current location matches the scheduled duration, otherwise locking out access to the clinical data recording functions and transmitting an exception report to a third party.

13. The system according to claim 11, wherein the location determining circuitry determines the current location by communicating with a global positioning system.

14. A method, performed by a provider electronic device, of securing access to and recording of healthcare information related to a healthcare intervention, the method comprising:
enabling a software lock that prohibits a healthcare provider from using the electronic device to access, receive, or transmit any healthcare information concerning a patient's healthcare intervention;
receiving, by a provider electronic device held by a healthcare provider and having an associated provider identification (ID) that identifies the healthcare provider, a patient ID that identifies a patient, from a wireless identification enabled object held by the patient;
retrieving, from a database, healthcare intervention data that includes expected time criteria, an expected patient ID, and an expected provider ID for a healthcare intervention to be performed on an expected patient associated with the expected patient ID;
receiving a time signal that identifies a current time; and
maintaining the software lock on the electronic device that prevents recording of clinical data if the expected patient ID does not match the received patient ID, the expected provider ID does not match the stored provider ID, or the current time is not consistent the expected time criteria; and disengaging the software lock on the electronic device to permit the recording of clinical data and completion of the healthcare intervention only if the expected patient ID matches the received patient ID, the expected provider ID matches the stored provider ID, and the current time is consistent the expected time criteria.

15. The method of claim 14, wherein the healthcare intervention data further includes expected location criteria identifying where the healthcare intervention is to be performed, the method further comprising:

receiving, from global positioning system (GPS) circuitry associated with the provider electronic device, a location signal that identifies a current location of the provider electronic device;

maintaining the software lock on the electronic device that prevents recording of clinical data if the current location is not consistent with the expected location criteria; and disengaging the software lock on the electronic device to permit the recording of clinical data and completion of the healthcare intervention only if the expected patient ID matches the received patient ID, the expected provider ID matches the stored provider ID, the current time is consistent the expected time criteria, and the current location is consistent with the expected location criteria.

16. The method of claim 14 further comprising:

generating an exception report if the received patient ID does not match the expected patient ID, the provider ID associated with the provider electronic device does not match the expected provider ID, the current location is not within the expected location criteria, or the current time is not within the expected time criteria; and generating a message that informs a third party of the exception report.

17. The method according to claim 14, wherein the expected time criteria includes a scheduled time, a scheduled duration, and a scheduled location for the scheduled healthcare intervention.

18. The method according to claim 17 further comprising:

generating an exception report if the scheduled time from the healthcare intervention data does not match the current time; and generating a message that informs a third party of the exception report.

19. The method according to claim 17 further comprising:

determining, by the provider electronic device, a current location of the provider electronic device; and generating an exception report if the current location does not match the scheduled location from the healthcare intervention data; and generating a message that informs a third party of the exception report.

20. The method according to claim 17 further comprising, after disengaging the software lock:

periodically determining, by the provider electronic device, a current duration for the scheduled healthcare intervention;

generating an exception report if the current duration is longer than the scheduled duration; and generating a message that informs a third party of the exception report.

* * * * *